(12) United States Patent
Maruyama

(10) Patent No.: US 10,123,780 B2
(45) Date of Patent: Nov. 13, 2018

(54) MEDICAL IMAGE DIAGNOSIS APPARATUS, IMAGE PROCESSING APPARATUS, AND IMAGE PROCESSING METHOD

(71) Applicant: Toshiba Medical Systems Corporation, Otawara-shi (JP)

(72) Inventor: Toshie Maruyama, Yaita (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 551 days.

(21) Appl. No.: 14/616,216

(22) Filed: Feb. 6, 2015

(65) Prior Publication Data

US 2015/0150537 A1 Jun. 4, 2015

Related U.S. Application Data

(63) Continuation of application No. PCT/JP2013/071561, filed on Aug. 8, 2013.

(30) Foreign Application Priority Data

Aug. 8, 2012 (JP) .................................. 2012-176323

(51) Int. Cl.
*A61B 5/00* (2006.01)
*A61B 8/08* (2006.01)
(Continued)

(52) U.S. Cl.
CPC .............. *A61B 8/523* (2013.01); *A61B 5/055* (2013.01); *A61B 5/4312* (2013.01); *A61B 6/466* (2013.01);
(Continued)

(58) Field of Classification Search
None
See application file for complete search history.

(56) References Cited

U.S. PATENT DOCUMENTS

2005/0020878 A1* 1/2005 Ohnishi ............. A61B 1/00009
600/117
2006/0228012 A1* 10/2006 Masuzawa ............ G06T 11/008
382/131
(Continued)

FOREIGN PATENT DOCUMENTS

JP 2006-288495 A 10/2006
JP 2009-056143 A 3/2009
(Continued)

OTHER PUBLICATIONS

International Search Report dated Oct. 8, 2013 for PCT/JP2013/071561 filed Aug. 8, 2013 with English Translation.
(Continued)

*Primary Examiner* — Joel F Brutus
(74) *Attorney, Agent, or Firm* — Oblon, McClelland, Maier & Neustadt, L.L.P.

(57) ABSTRACT

A medical image diagnosis apparatus according to an embodiment includes a lumen image generating unit, a running line generating unit, an image synthesizing unit and a control unit. The lumen image generating unit generates a lumen image depicting a shape of a lumen having a branch based on volume data. The running line generating unit generates a plurality of running lines based on the shape of the lumen. The image synthesizing unit generates a synthetic image by superimposing, on the lumen image, the plurality of running lines indicating moving paths of a viewpoint in a virtual endoscopy image. The control unit displays the synthetic image and controls the image synthesizing unit to perform depiction that distinguishes between a range of a running line along which a virtual endoscopy image is displayed and a range of a running line along which no virtual endoscopy image is displayed.

14 Claims, 16 Drawing Sheets

(51) Int. Cl.
  *A61B 5/055* (2006.01)
  *A61B 8/14* (2006.01)
  *A61B 6/00* (2006.01)
  *G06T 19/00* (2011.01)
  *A61B 8/00* (2006.01)
  *A61B 6/03* (2006.01)

(52) U.S. Cl.
  CPC ............ *A61B 6/502* (2013.01); *A61B 6/5223* (2013.01); *A61B 8/0825* (2013.01); *A61B 8/0891* (2013.01); *A61B 8/14* (2013.01); *A61B 8/483* (2013.01); *G06T 19/006* (2013.01); A61B 6/032 (2013.01); A61B 8/463 (2013.01); A61B 8/481 (2013.01); A61B 8/488 (2013.01); G06T 2210/41 (2013.01)

(56) References Cited

U.S. PATENT DOCUMENTS

| | | | | |
|---|---|---|---|---|
| 2006/0229513 | A1* | 10/2006 | Wakai | G06T 5/50 600/407 |
| 2007/0161853 | A1* | 7/2007 | Yagi | A61B 1/00009 600/109 |
| 2009/0292171 | A1* | 11/2009 | Ito | A61B 1/00009 600/111 |
| 2011/0018871 | A1* | 1/2011 | Shirahata | A61B 8/00 345/419 |
| 2011/0255755 | A1 | 10/2011 | Shirahata et al. | |
| 2012/0287238 | A1* | 11/2012 | Onishi | A61B 1/0005 348/45 |

FOREIGN PATENT DOCUMENTS

| | | |
|---|---|---|
| WO | WO 2010/074058 A1 | 7/2010 |
| WO | WO 2012/101888 A1 | 8/2012 |

OTHER PUBLICATIONS

International Written Opinion dated Oct. 8, 2013 for PCT/JP2013/071561 filed Aug. 8, 2013.

Takeaki Kurita, "Virtual Mammaryendoscopy of Ultrasound Image Using 4D Probe", Japanese Journal of Medical Ultrasonics in Medicine, Shoichi Senda, Apr. 15, 2011, S447 with English Translation.

Yuichiro Hayashi, "Development of a Function for Identifying Novisualized Regions in a Virtual Endoscope System", Medical Imaging Technology, vol. 20, No. 5, Sep. 2002, JAMIT, Sep. 25, 2002, 562-571 with partial English Translation.

\* cited by examiner

Observation of all running lines is not completed yet!
Is it OK to terminate processing?

MEDICAL IMAGE DIAGNOSIS APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2013/071561 filed on Aug. 8, 2013 which designates the United States, incorporated herein by reference, and which claims the benefit of priority from Japanese Patent Application No. 2012-176323, filed on Aug. 8, 2012, the entire contents of which are incorporated herein by reference.

FIELD

Embodiments described herein relate generally to a medical image diagnosis apparatus, an image processing apparatus, and an image processing method.

BACKGROUND

Conventionally, medical image diagnosis apparatuses, such as ultrasonic diagnosis apparatuses, X-ray computed tomography (CT) apparatuses, and magnetic resonance imaging (MRI) apparatuses, have been in practical use, including apparatuses capable of generating three-dimensional medical image data (hereinafter, referred to as volume data). In recent years, virtual endoscopy (VE) images with which the inside of a lumen can be observed are generated and displayed from volume data including the lumen. Examples of the method for displaying such a virtual endoscopy image include displaying the virtual endoscopy image as a moving image by moving a viewpoint along a running line (a core line) of the lumen. Hereinafter, such display is referred to as "display of a VE moving image".

For example, a VE moving image of a mammary gland is display by ultrasonic diagnosis apparatuses, which are used for examinations and diagnoses of various types of body tissues because they have advantageous effects, such as non-invasive characteristics, compared to other medical image diagnosis apparatuses. Display of a VE moving image of a mammary gland is a function expected to serve as a virtual mammary duct endoscopy. Because of structural characteristics of a mammary gland, a plurality of mammary ducts are present in volume data including the mammary gland and each branch off repeatedly.

In an actual mammary duct endoscopy, an endoscope is inserted into a mammary duct that secretes milk, and all the branches included in the mammary duct are observed, by which it is identified which branch secretes the milk. In other words, in an actual mammary duct endoscopy, an examiner repeats an operation of moving the endoscope back to a branch point, thereby observing all the branches. Similarly to this, it is necessary to observe all the branches included in a mammary duct that secretes milk also in a virtual mammary duct endoscopy.

In conventional display of a VE moving image, however, an examiner typically refers to a multi-planer reconstruction (MPR) image obtained by cutting volume data along a section passing through a position of a viewpoint, thereby detecting a current viewpoint position of the virtual endoscopy image, for example. In other words, in the conventional display of a VE moving image, the relation between the entire structure of a mammary duct and the current viewpoint position and determination to complete the observation depend on memory of the examiner. As a result, in an examination carried out by the conventional display of a VE moving image, the examination may possibly be completed despite the presence of yet-to-be-observed branches because of an oversight or a misunderstanding of the examiner.

The possibility that the examination may be completed despite the presence of yet-to-be-observed branches typically occurs in display of a VE moving image of a branching lumen. Furthermore, the possibility that the examination may be completed despite the presence of yet-to-be-observed branches also occurs in the use of volume data acquired by a medical image diagnosis apparatus other than ultrasonic diagnosis apparatuses.

DETAILED DESCRIPTION

A medical image diagnosis apparatus according to an embodiment includes a lumen image generating unit, a running line generating unit, an image synthesizing unit and a control unit. The lumen image generating unit generates a lumen image depicting a shape of a lumen having a branch based on volume data that is three-dimensional medical image data. The running line generating unit generates a plurality of running lines based on the shape of the lumen having the branch. The image synthesizing unit generates a synthetic image by superimposing, on the lumen image, the plurality of the running lines indicating moving paths of a viewpoint in a virtual endoscopy image of the lumen having the branch. The control unit displays the synthetic image on a certain display unit. The control unit controls the image synthesizing unit so as to perform depiction that distinguishes between a range of a running line along which a virtual endoscopy image is displayed and a range of a running line along which no virtual endoscopy image is displayed.

Exemplary embodiments of a medical image diagnosis apparatus are described below in detail with reference to the accompanying drawings. An ultrasonic diagnosis apparatus, which is a medical image diagnosis apparatus, is described below as an embodiment.

Embodiments

Figure 1:
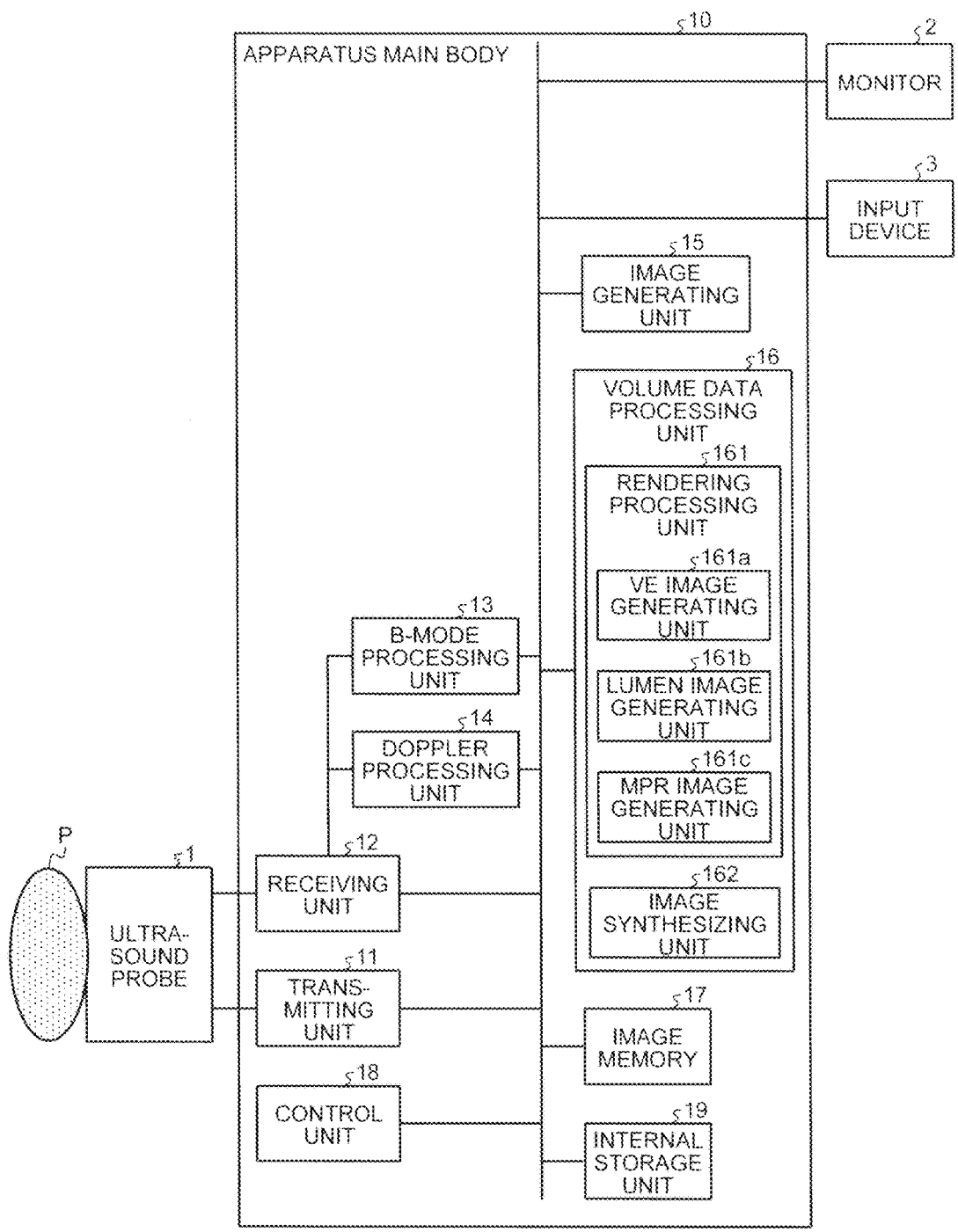
FIG. 1 is a block diagram of an exemplary configuration of an ultrasonic diagnosis apparatus according to an embodiment.

The configuration of an ultrasonic diagnosis apparatus according to an embodiment will be described. FIG. 1 is a block diagram of an exemplary configuration of an ultrasonic diagnosis apparatus according to the present embodiment. As illustrated in FIG. 1, the ultrasonic diagnosis apparatus according to the present embodiment includes an ultrasound probe 1, a monitor 2, an input device 3, and an apparatus main body 10.

The ultrasound probe 1 includes a plurality of piezoelectric transducer elements. The plurality of the piezoelectric transducer elements generate ultrasonic waves based on a driving signal supplied from a transmitting unit 11 included in the apparatus main body 10, which will be described later. The ultrasound probe 1 receives reflected waves from a subject P and converts the reflected waves into an electrical signal. The ultrasound probe 1 further includes a matching layer provided to the piezoelectric transducer elements and a backing member that prevents ultrasonic waves from traveling rearward from the piezoelectric transducer elements. The ultrasound probe 1 is connected to the apparatus main body 10 in an attachable and detachable manner.

When ultrasonic waves are transmitted from the ultrasound probe 1 to the subject P, the ultrasonic waves thus transmitted are sequentially reflected at a surface of discontinuity of acoustic impedance in a body tissue of the subject P. The ultrasonic waves are received by the piezoelectric transducer elements included in the ultrasound probe 1 as a reflected wave signal. The amplitude of the reflected wave signal thus received depends on difference in the acoustic impedance on the discontinuous surface on which the ultrasonic waves are reflected. A reflected wave signal obtained when the ultrasonic pulse thus transmitted is reflected by a moving bloodstream, the surface of a cardiac wall, or the like depends on a velocity component of the moving object with respect to an ultrasonic-wave transmitting direction to undergo frequency shift because of the Doppler effect.

The ultrasound probe 1 according to the present embodiment is an ultrasound probe that can scan the subject P two-dimensionally and scan the subject P three-dimensionally with ultrasonic waves. Specifically, the ultrasound probe 1 according to the first embodiment is a mechanical scanning probe that scans the subject P two-dimensionally using the piezoelectric transducer elements arranged in a line and scans the subject P three-dimensionally by oscillating the plurality of the piezoelectric transducer elements at a certain angle (an oscillation angle). Alternatively, the ultrasound probe 1 according to the first embodiment is a two-dimensional ultrasound probe that can perform ultrasound scanning on the subject P three-dimensionally by arranging the plurality of the piezoelectric transducer elements in a matrix. The two-dimensional ultrasound probe can also scan the subject P two-dimensionally by focusing and transmitting the ultrasonic waves.

The input device 3 includes a mouse, a keyboard, a button, a panel switch, a touch command screen, a foot switch, a trackball, and a joystick, for example. The input device 3 receives various types of setting requests from an operator of the ultrasonic diagnosis apparatus and transfers the various types of setting requests thus received to the apparatus main body 10.

The monitor 2 displays a graphical user interface (GUI) through which the operator of the ultrasonic diagnosis apparatus inputs various types of setting request with the input device 3 and an ultrasonic image generated in the apparatus main body 10, for example.

The apparatus main body 10 is an apparatus that generates ultrasonic image data based on reflected waves received by the ultrasound probe 1. Specifically, the apparatus main body 10 according to the first embodiment is an apparatus that can generate three-dimensional ultrasonic image data based on three-dimensional reflected wave data received by the ultrasound probe 1. Hereinafter, the three-dimensional ultrasonic image data is referred to as "volume data".

As illustrated in FIG. 1, the apparatus main body 10 includes a transmitting unit 11, a receiving unit 12, a B-mode processing unit 13, a Doppler processing unit 14, an image generating unit 15, a volume data processing unit 16, an image memory 17, a control unit 18, and an internal storage unit 19.

The transmitting unit 11 includes a pulse generator, a transmission delay unit, and a pulser, for example, and supplies a driving signal to the ultrasound probe 1. The pulse generator repeatedly generates a rate pulse that forms transmission ultrasonic waves at a certain rate frequency. The transmission delay unit supplies delay times required for the respective piezoelectric transducer elements to focus ultrasonic waves generated from the ultrasound probe 1 into a beam and to determine the transmission directivity to the respective rate pulses generated by the pulse generator. The pulser applies a driving signal (a driving pulse) to the ultrasound probe 1 at a timing based on the rate pulse. Specifically, the transmission delay unit changes the delay times supplied to the respective rate pulses, thereby arbitrarily adjusting the direction of transmission of the ultrasonic waves transmitted from the piezoelectric transducer element surface.

The transmitting unit 11 has a function to instantaneously change a transmission frequency, a transmission driving voltage, and the like so as to perform a certain scanning sequence based on an instruction issued from the control unit 18, which will be described later. Specifically, change of the transmission driving voltage is performed by a linear-amplifier oscillator circuit that can instantaneously change the value of the voltage or a mechanism that electrically switches a plurality of power-supply units.

The receiving unit 12 includes a pre-amplifier, an analog/digital (A/D) converter, a reception delay unit, and an adder, for example. The receiving unit 12 performs various types of processing on a reflected wave signal received by the ultrasound probe 1, thereby generating reflected wave data. The pre-amplifier amplifies a reflected wave signal on each channel. The A/D converter performs A/D conversion on the reflected wave signal thus amplified. The reception delay unit supplies a delay time required to determine the reception directivity. The adder performs addition processing on the reflected wave signal processed by the reception delay unit, thereby generating reflected wave data. The addition processing of the adder emphasizes a reflection component in a direction corresponding to the reception directivity of the reflected wave signal. Based on the reception directivity and the transmission directivity, a synthetic beam for transmission and reception of ultrasonic waves is formed.

To scan the subject P three-dimensionally, the transmitting unit 11 according to the present embodiment causes the ultrasound probe 1 to transmit a three-dimensional ultrasonic beam. The receiving unit 12 according to the present embodiment generates three-dimensional reflected wave data from a three-dimensional reflected wave signal received by the ultrasound probe 1.

Various forms may be selected as the form of an output signal from the receiving unit 12, including a signal containing phase information, which is called a radio frequency (RF) signal, and amplitude information obtained after envelope detection is performed, for example.

The B-mode processing unit 13 receives reflected wave data from the receiving unit 12. The B-mode processing unit 13 performs logarithmic amplification, envelope detection, and other processing on the reflected wave data, thereby generating data (B-mode data) in which the signal intensity is depicted by the intensity of brightness.

The Doppler processing unit 14 performs a frequency analysis on reflected wave data received from the receiving unit 12 to extract velocity information from the reflected wave data. The Doppler processing unit 14 extracts a bloodstream and a tissue by the Doppler effect and a contrast medium echo component and generates data (Doppler data) by extracting moving object information, such as average velocity, dispersion, and power, at multiple points.

The B-mode processing unit 13 and the Doppler processing unit 14 according to the present embodiment can process both two-dimensional reflected wave data and three-dimensional reflected wave data. In other words, the B-mode processing unit 13 generates two-dimensional B-mode data from two-dimensional reflected wave data and generates three-dimensional B-mode data from three-dimensional reflected wave data. The Doppler processing unit 14 generates two-dimensional Doppler data from two-dimensional reflected wave data and generates three-dimensional Doppler data from three-dimensional reflected wave data.

The image generating unit 15 generates ultrasonic image data from the data generated by the B-mode processing unit 13 and the Doppler processing unit 14. In other words, the image generating unit 15 generates B-mode image data depicting the intensity of reflected waves by the brightness from two-dimensional B-mode data generated by the B-mode processing unit 13. Furthermore, the image generating unit 15 generates an average velocity image, a dispersion image, and a power image depicting the moving object information or color Doppler image data serving as a combination image of these images from two-dimensional Doppler data generated by the Doppler processing unit 14.

Typically, the image generating unit 15 converts (scan-converts) a scanning-line signal row in ultrasonic scanning into a scanning-line signal row in a video format represented by television and the like, thereby generating ultrasonic image data for display. Specifically, the image generating unit 15 performs coordinate transformation based on a mode of ultrasonic scanning performed by the ultrasound probe 1, thereby generating ultrasonic image data for display. Furthermore, the image generating unit 15 synthesizes character information of various types of parameters, a scale, a body mark, and the like on the ultrasonic image data.

The image generating unit 15 performs coordinate transformation on three-dimensional B-mode data generated by the B-mode processing unit 13, thereby generating three-dimensional B-mode image data. Furthermore, the image generating unit 15 performs coordinate transformation on three-dimensional Doppler data generated by the Doppler processing unit 14, thereby generating three-dimensional color Doppler image data. In other words, the image generating unit 15 generates "three-dimensional B-mode image data and three-dimensional color Doppler image data" as "volume data that is three-dimensional ultrasonic image data".

The volume data processing unit 16 generates ultrasonic image data for display from the volume data generated by the image generating unit 15. As illustrated in FIG. 1, the volume data processing unit 16 includes a rendering processing unit 161 and an image synthesizing unit 162.

The rendering processing unit 161 is a processing unit that performs rendering processing on volume data so as to generate various types of images (two-dimensional images) for displaying the volume data on the monitor 2.

Examples of the rendering processing performed by the rendering processing unit 161 include processing for generating a multi-planer reconstruction (MPR) image from volume data by performing MPR. Examples of the rendering processing performed by the rendering processing unit 161 further include processing for performing "curved MPR" for specifying a curved plane with respect to a Cartesian coordinate system of volume data and reconstructing a section on the curved plane and processing for performing "Intensity Projection" on volume data. Examples of the rendering processing performed by the rendering processing unit 161 further include volume rendering (VR) processing for generating a two-dimensional image (a volume rendering image) reflecting three-dimensional information.

The rendering processing unit 161 according to the present embodiment includes a virtual endoscopy (VE) image generating unit 161a, a lumen image generating unit 161b, and an MPR image generating unit 161c serving as processing units that displays a virtual endoscopy image (e.g., display of a VE moving image).

The virtual endoscopy image generating unit 161a, for example, performs perspective projection as volume rendering processing, thereby generating a virtual endoscopy image with which the inside of a lumen can be observed stereoscopically from volume data including the lumen. The lumen image generating unit 161b generates a lumen image with which a lumen can be viewed stereoscopically in a cavity mode for performing black-and-white inversion on the brightness value in volume data including the lumen. The MPR image generating unit 161c generates an MPR image from volume data including a lumen.

Figure 2:
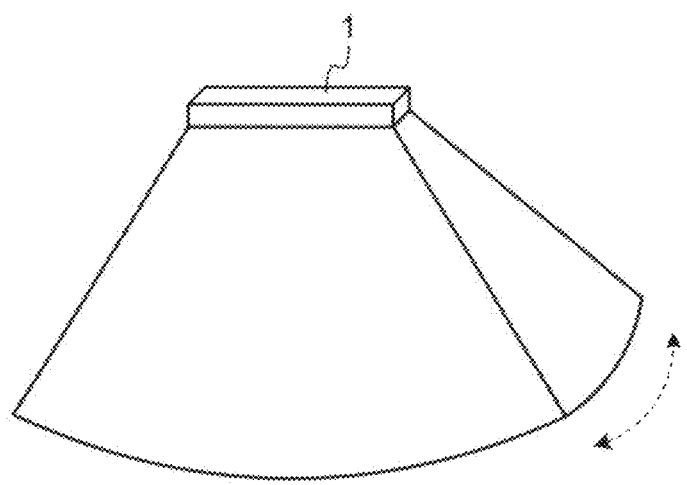
FIG. 2 is a view for explaining an A surface, a B surface, and a C surface.
Figure 2:
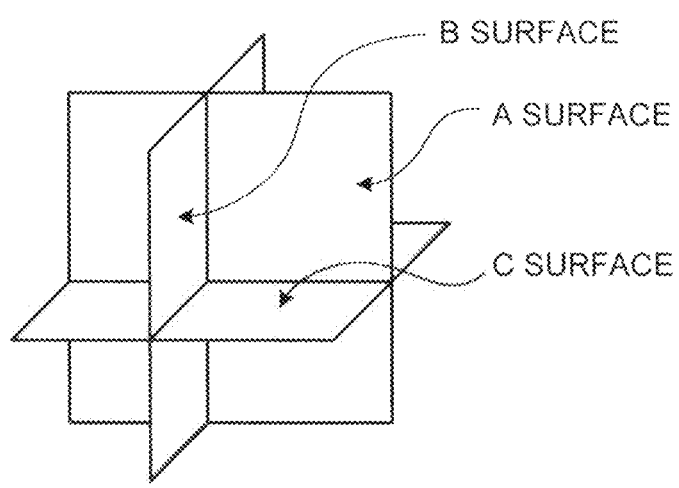

The following describes three types of sections (an A surface, a B surface, and a C surface) typically used to generate MPR images from volume data in the ultrasonic diagnosis apparatus with reference to FIG. 2. FIG. 2 is a view for explaining the A surface, the B surface, and the C surface, which are used in the ultrasound probe 1, which is a mechanical scanning probe that mechanically oscillates. As illustrated in FIG. 2, the A surface is a section formed by an alignment direction of the piezoelectric transducer elements in the ultrasound probe 1 and a transmission direction of ultrasonic waves. As illustrated in FIG. 2, the B surface is a section formed by the transmission direction of the ultrasonic waves and an oscillation direction. As illustrated in FIG. 2, the C surface is a section extending in a direction perpendicular to the transmission direction of the ultrasonic waves. If the ultrasound probe 1 is a two-dimensional ultrasound probe, the A surface and the B surface are defined as two sections formed by two respective alignment directions of the piezoelectric transducer elements and the transmission direction of the ultrasonic waves.

The image synthesizing unit 162 illustrated in FIG. 1 synthesizes various two-dimensional images generated by the rendering processing unit 161 in a certain layout and synthesizes information superimposed on the two-dimensional images. The image synthesizing unit 162 then outputs the image thus synthesized to the monitor 2. The processing performed by the rendering processing unit 161 and the image synthesizing unit 162 to display a VE moving image in the present embodiment, for example, will be described later in detail.

The image memory 17 is a memory that stores therein image data for display generated by the image generating unit 15 and the volume data processing unit 16. The image memory 17 can also store therein data generated by the B-mode processing unit 13 and the Doppler processing unit 14. The B-mode data and the Doppler data stored in the image memory 17 can be retrieved by the operator after a diagnosis, for example. The B-mode data and the Doppler data are each converted into an ultrasonic image for display via the image generating unit 15 and the volume data processing unit 16.

The internal storage unit 19 stores therein a control program for performing transmission and reception of ultrasonic waves, image processing, and display processing, and various types of data, such as diagnosis information (e.g., a patient ID and findings of a doctor), a diagnosis protocol, and various types of body marks. Furthermore, the internal storage unit 19 is used to retain image data stored in the image memory 17 as needed, for example.

The control unit 18 controls the entire processing of the ultrasonic diagnosis apparatus. Specifically, the control unit 18 controls the processing of the transmitting unit 11, the receiving unit 12, the B-mode processing unit 13, the Doppler processing unit 14, the image generating unit 15, and the volume data processing unit 16 based on various types of setting requests received from the operator via the input device 3 and various types of control program and various types of data read from the internal storage unit 19. Furthermore, the control unit 18 performs control such that the monitor 2 displays ultrasonic image data for display stored in the image memory 17 and the internal storage unit 19.

The entire configuration of the ultrasonic diagnosis apparatus according to the present embodiment has been described. With this configuration, the ultrasonic diagnosis apparatus according to the present embodiment moves a viewpoint along a running line (a core line) of a lumen, thereby displaying a VE moving image, that is, displaying a virtual endoscopy image as a moving image. The ultrasonic diagnosis apparatus according to the present embodiment, for example, performs three-dimensional scanning on an area including a mammary gland, thereby generating volume data relating to the mammary gland, that is, volume data including the mammary gland in a virtual mammary duct endoscopy. The ultrasonic diagnosis apparatus according to the present embodiment uses the volume data including the mammary gland to display a VE moving image of the mammary gland. In a virtual mammary duct endoscopy, it is necessary to observe all the branches included in mammary ducts that secrete milk in accordance with an examination standard.

Because of structural characteristics of a mammary gland, however, a plurality of mammary ducts are present in volume data including the mammary gland and each of the mammary ducts branches off repeatedly.

In a conventional display of a VE moving image, an operator (an examiner) typically refers to MPR images obtained by cutting volume data along three sections (the A surface, the B surface, and the C surface) passing through a position of a viewpoint, thereby detecting a current viewpoint position of the virtual endoscopy image, for example. As a result, in an examination carried out by the conventional display of a VE moving image, the examination may possibly be completed despite the presence of yet-to-be-observed branches because of an oversight or a misunderstanding of the examiner. Furthermore, in the conventional display of a VE moving image, the moving direction of the viewpoint along a running line may be determined by automatic search or instructing manually. In these methods, however, it is difficult for the operator to grasp which branch of which mammary duct has been observed. As such, in the conventional display of a VE moving image of a mammary gland, the examination may possibly be completed despite the presence of yet-to-be-observed branches. The possibility that the examination may be completed despite the presence of yet-to-be-observed branches occurs in general in displaying a VE moving image of a branching lumen.

Therefore, the ultrasonic diagnosis apparatus according to the present embodiment displays information that can facilitate the operator's grasping of completion of observation of a lumen having branches by processing performed by the volume data processing unit 16 under the control of the control unit 18, which will be described below in detail.

Figure 3A:
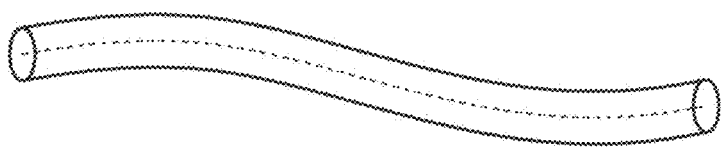
FIG. 3A and FIG. 3B are views for explaining an example of processing of a virtual endoscopy image generating unit.
Figure 3B:
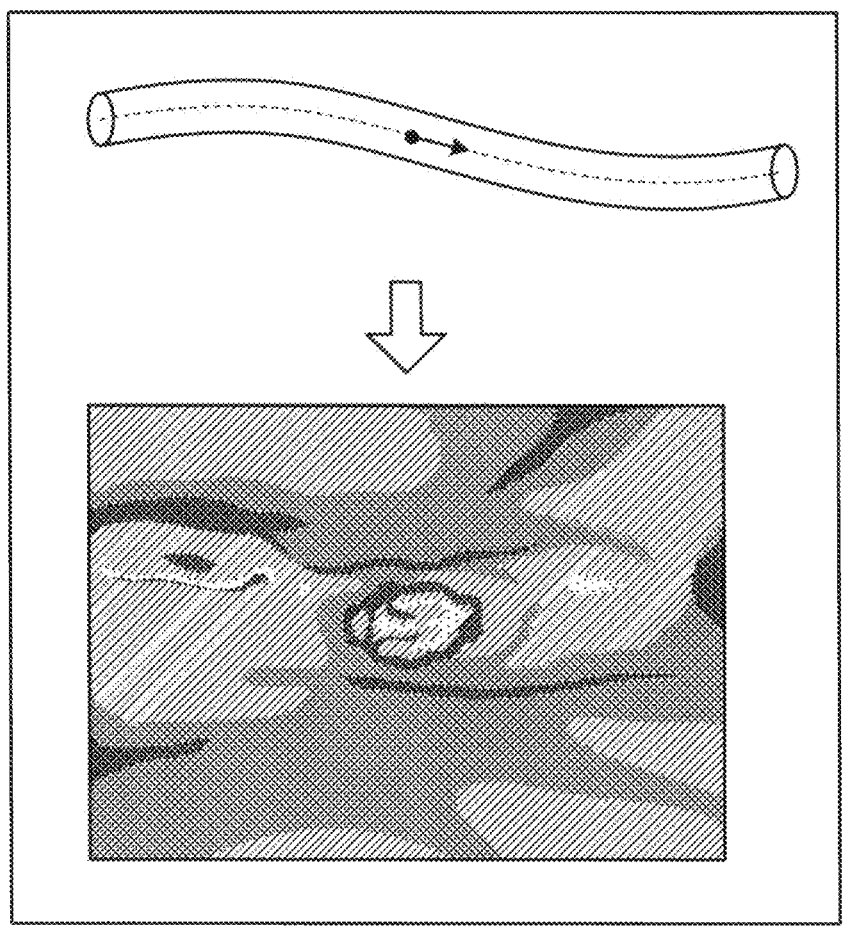

An example of the processing performed by the rendering processing unit 161 in the present embodiment will now be described in detail. As described above, the virtual endoscopy image generating unit 161a generates a virtual endoscopy image of a lumen included in volume data. In the present embodiment, the virtual endoscopy image generating unit 161a generates a virtual endoscopy image of a lumen of a mammary gland. Specifically, the virtual endoscopy image generating unit 161a extracts an area of a lumen included in volume data. FIG. 3A and FIG. 3B are views for explaining an example of the processing of the virtual endoscopy image generating unit.

The virtual endoscopy image generating unit 161a, for example, extracts pixels (voxels) having a brightness value corresponding to that of the lumen, thereby extracting a lumen area. The virtual endoscopy image generating unit 161a, for example, performs thinning processing on the lumen area thus extracted, thereby extracting a running line (a core line) of the lumen as illustrated in FIG. 3A. The running line is depicted by a dotted line in FIG. 3A. The virtual endoscopy image generating unit 161a generates a virtual endoscopy image from a viewpoint set on the running line by perspective projection as illustrated in FIG. 3B, for example. In FIG. 3B, the virtual endoscopy image is generated in a visual line direction toward the right from one viewpoint on the running line. To perform the perspective projection, a view angle is set besides the position of the viewpoint and the visual line direction.

The virtual endoscopy image generating unit 161a extracts a branching lumen area from volume data including a lumen having branches. The virtual endoscopy image generating unit 161a extracts a running line branching off at a plurality of branch points from the branching lumen area. In other words, the virtual endoscopy image generating unit 161a has a function of a running line generating unit that generates a plurality of running lines based on the shape of the lumen having the branch. The virtual endoscopy image generating unit 161a, for example, extracts a plurality of branching mammary duct areas from volume data including a mammary gland. The virtual endoscopy image generating unit 161a further extracts a running line branching off at a plurality of branch points from the respective mammary duct areas. A running line of a main duct branches off into two running lines of first branches at a first branch point, for example. Furthermore, the running lines of the first branches each branch off into two running lines of second branches at a second branch point, for example. The number of moving paths of a viewpoint in which VE moving image display should be performed in a lumen having branches is plural in a case of one lumen. The main duct described above is also referred to as a responsible mammary duct. A plurality of responsible mammary ducts is present in a breast. The virtual endoscopy image generating unit 161a serving as the running line generating unit extracts a "running line branching off at a plurality of branch points" from the respective responsible mammary ducts.

Figure 4A:
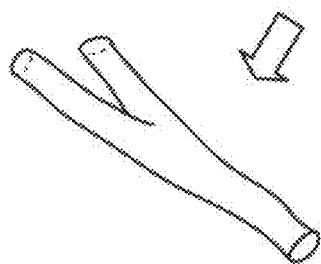
FIG. 4A and FIG. 4B are views for explaining an example of processing of a lumen image generating unit.
Figure 4B:

The lumen image generating unit 161b generates a lumen image depicting a shape of a lumen having a branch based on volume data. The lumen image generating unit 161b generates a lumen image depicting a shape of a branching lumen included in volume data. In the present embodiment, the lumen image generating unit 161b generates a lumen image depicting the shape of a lumen of a mammary gland having branches based on volume data relating to the mammary gland. In the present embodiment, as described above, the lumen image generating unit 161b generates a lumen image with which the branching lumen can be viewed stereoscopically in the cavity mode for performing black-and-white inversion of the brightness value in volume data including the lumen. In three-dimensional B-mode image data, a pixel in the lumen has a low brightness value. By using volume data after inversion whose brightness value of the volume data including the lumen is black-and-white inverted, an area in the lumen is displayed with high brightness in the lumen image. FIGS. 4A and 4B are views for explaining an example of the processing of the lumen image generating unit. In the cavity mode, target voxels may be narrowed down to perform rendering such that only a high-brightness area adjacent to the core line thus extracted is rendered.

As illustrated in FIG. 4A, the lumen image generating unit 161b performs volume rendering processing on the volume data subjected to the inversion based on the position of the viewpoint and the visual line direction specified by the operator. Thus, the lumen image generating unit 161b generates a lumen image depicting a lumen area brightly as illustrated in FIG. 4B. The lumen image illustrated in FIG. 4B depicts the shape of two mammary ducts and the shape of branches included in the respective mammary ducts.

The operator changes the position of the viewpoint and the visual line direction for generating the lumen image, thereby viewing the shape of the lumen included in the volume data from various positions and directions. The operator can change the position of the viewpoint and the visual line direction for generation of the lumen image by operating the mouse and the trackball of the input device 3, for example. The lumen image used in the present embodiment may be an image extending a shape of a lumen two-dimensionally so as to depict the entire state of the branches included in the lumen.

Figure 5:
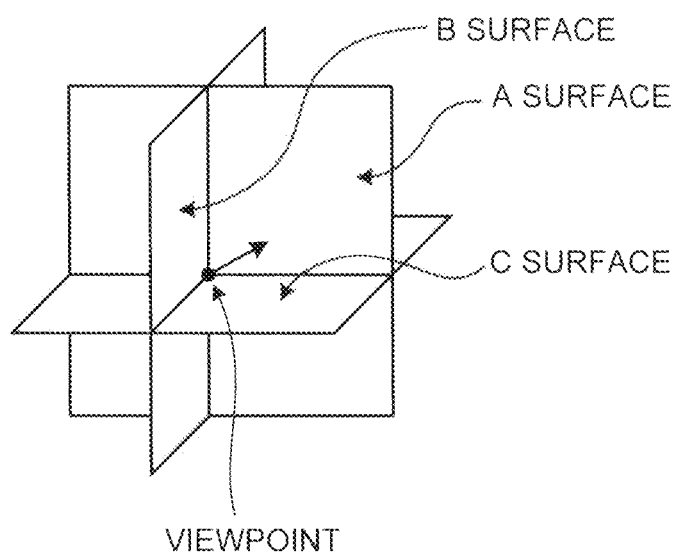
FIG. 5 is a view for explaining an example of processing of an MPR image generating unit.

The MPR image generating unit 161c generates an MPR image from volume data including a lumen as described above. FIG. 5 is a view for explaining an example of the processing of the MPR image generating unit. Specifically, when performing display of a VE moving image, the MPR image generating unit 161c generates MPR images of the A surface, the B surface, and the C surface passing through the position of the viewpoint used for generation of a virtual endoscopy image to be displayed from the volume data including the lumen as illustrated in FIG. 5. The image synthesizing unit 162 illustrated in FIG. 1 superimposes an image indicating information of the position of the viewpoint and the visual line direction used for generation of the virtual endoscopy image on the MPR images of the A surface, the B surface, and the C surface as illustrated in FIG. 5.

Figure 6A:
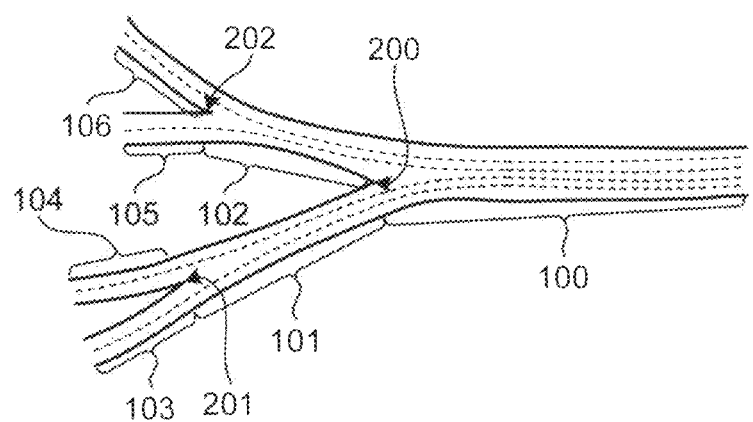
FIG. 6A and FIG. 6B are views for explaining an example of a synthetic image generated by an image synthesizing unit.
Figure 6B:

The image synthesizing unit 162 according to the present embodiment generates a synthetic image by superimposing, on the lumen image, a plurality of running lines indicating moving paths of a viewpoint in a virtual endoscopy image of the lumen having a branch. The running lines serve as the moving paths of the viewpoint used to display the virtual endoscopy image of the lumen having a branch. In the present embodiment, the running lines serve as the moving paths of the viewpoint used to display the virtual endoscopy image of the lumen having branches as a moving image. The image synthesizing unit 162, for example, divides a "running line branching off repeatedly" extracted by the virtual endoscopy image generating unit 161a into a plurality of running lines serving as the moving paths of the viewpoint based on information, such as the number of branches. The image synthesizing unit 162 then generates a synthetic image by superimposing, on the lumen image, the plurality of the running lines thus branching off. FIGS. 6A and 6B are views for explaining an example of the synthetic image generated by the image synthesizing unit.

FIG. 6A schematically illustrates the synthetic image generated by the image synthesizing unit 162. A main duct 100 of a lumen (a mammary duct) illustrated in FIG. 6A branches into a first branch 101 and a first branch 102 at a first branch point 200. The main duct 100 corresponds to a responsible mammary duct. The first branch 101 illustrated in FIG. 6A branches into a second branch 103 and a second branch 104 at a second branch point 201. The first branch 102 illustrated in FIG. 6A branches into a second branch 105 and a second branch 106 at a second branch point 202. Specifically, in the lumen including the main duct 100, the moving paths of the viewpoint required for observation in display of the VE moving image are the following four paths: a path of "the main duct 100, the first branch 101, and the second branch 103"; a path of "the main duct 100, the first branch 101, and the second branch 104"; a path of "the main duct 100, the first branch 102, and the second branch 105"; and a path of "the main duct 100, the first branch 102, and the second branch 106". The synthetic image of FIG. 6A illustrates the moving paths of the viewpoint in one responsible mammary duct (the main duct 100). The synthetic image of FIG. 6A actually depicts moving paths of the viewpoint in respective responsible mammary ducts.

The control unit 18 displays a synthetic image on the monitor 2 so as to enable the operator to grasp the moving path of the viewpoint in display of a VE moving image. When a running line branching off repeatedly is superimposed on a lumen image without any change, it is difficult for the operator to readily grasp the fact that the number of moving paths of the viewpoint is four, for example.

To address this, in the case where a running line branching off twice is extracted, for example, the image synthesizing unit 162 superimposes "2×2=4" running lines in the lumen of the lumen image as illustrated in FIG. 6A. The image synthesizing unit 162 generates the synthetic image under the control of the control unit 18 that acquires information relating to "the positions of the running lines in the lumen area, the positions of the branch points of the running lines in the lumen area, and the number of branch points of the running lines" from the virtual endoscopy image generating unit 161a.

FIG. 6B illustrates a synthetic image generated by the image synthesizing unit 162 superimposing a plurality of running lines on the lumen image illustrated in FIG. 4B. While the respective running lines are depicted by a dotted line, a chain line, a dashed-dotted line, and the like in the synthetic image illustrated in FIG. 6B for convenience of drawing, the running lines are actually depicted by respective dotted lines in different colors. Because the depiction method varies depending on the respective running lines, the operator can readily grasp the number of moving paths of the viewpoint.

To distinguish the running line extracted by the virtual endoscopy image generating unit 161a from the running line superimposed on the lumen image by the image synthesizing unit 162, the running line extracted by the virtual endoscopy image generating unit 161a may be hereinafter referred to as an "extracted running line" or a "moving path of the viewpoint".

Figure 7:
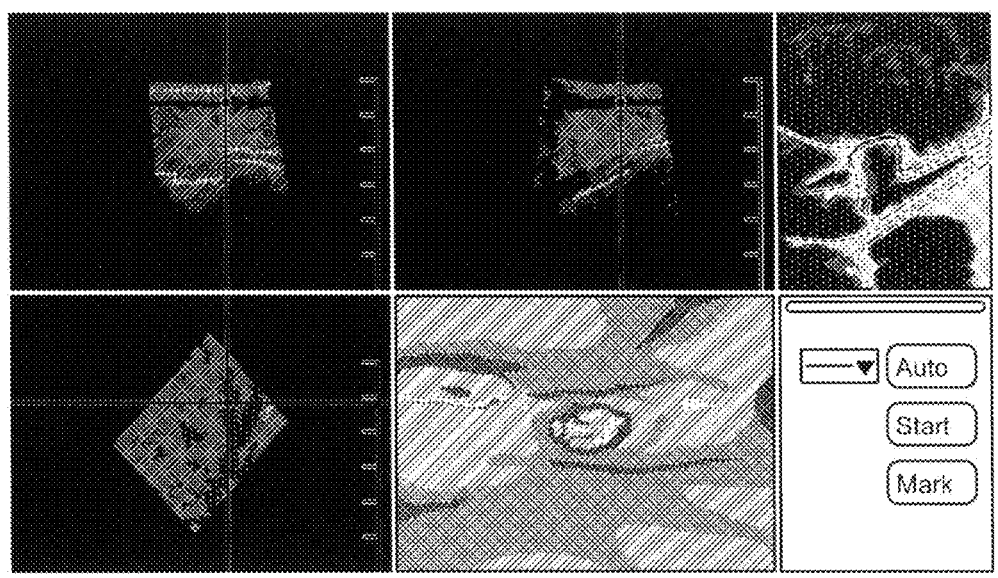
FIG. 7 is a view for explaining a display example of a synthetic image displayed by a control unit according to the present embodiment.

The control unit 18 displays a synthetic image as described above. FIG. 7 is a view for explaining a display example of the synthetic image displayed by the control unit according to the present embodiment. As illustrated in FIG. 7, the control unit 18 divides the display area of the monitor 2 into six display areas. The control unit 18 displays the MPR image (A surface) on the upper-left display area, displays the MPR image (B surface) on the upper-middle display area, and displays the MPR image (C surface) on the lower-left display area as illustrated in FIG. 7. The information of the position of the viewpoint and the visual line direction used for generation of the virtual endoscopy image is superimposed on the respective MPR images displayed in the three divided display areas as illustrated in FIG. 7 (refer to points and arrows in the figure).

The control unit 18 displays the virtual endoscopy image on the lower-middle display area and displays the synthetic image of the lumen image and the plurality of the running lines on the upper-right display area as illustrated in FIG. 7. Furthermore, the control unit 18 displays an operation menu used for fly-through display on the lower-right display area as illustrated in FIG. 7.

When volume data is specified and a request to start display of a VE moving image is received, the control unit 18 causes the virtual endoscopy image generating unit 161a to perform extraction processing of running lines, causes the lumen image generating unit 161b to perform generation processing of a lumen image, and causes the image synthesizing unit 162 to perform generation processing of a synthetic image. The control unit 18 causes the MPR image generating unit 161c to perform generation processing of three MPR images based on initial setting conditions and causes the virtual endoscopy image generating unit 161a to perform generation processing of a virtual endoscopy image based on the initial setting conditions.

The initial setting conditions are conditions in which the position of the viewpoint is set at the end on the main duct side of the longest extracted running line among the extracted running lines and the visual line direction is a direction toward the first branch point, for example. The view angle is arbitrarily set by the operator.

Thus, the monitor 2 displays an initial screen prior to start of the VE moving image in the layout illustrated in FIG. 7. The control unit 18, for example, controls display of the VE moving image based on various types of operations performed by the operator with the operation menu and the synthetic image displayed on the initial screen. The following describes display of a VE moving image performed by the control unit 18 according to the present embodiment in detail with reference to FIG. 8A, FIG. 8B, FIG. 8C, FIG. 9A, FIG. 9B, FIG. 10, FIG. 11, FIG. 12A, FIG. 12B, FIG. 12C, FIG. 13A, FIG. 13B, FIG. 13C, FIG. 14A, FIG. 14B, FIG. 15A and FIG. 15B. FIG. 8A, FIG. 8B, FIG. 8C, FIG. 9A, FIG. 9B, FIG. 10, FIG. 11, FIG. 12A, FIG. 12B, FIG. 12C, FIG. 13A, FIG. 13B, FIG. 13C, FIG. 14A, FIG. 14B, FIG. 15A and FIG. 15B are views for explaining control of display of a VE moving image performed by the control unit according to the present embodiment.

Figure 8A:
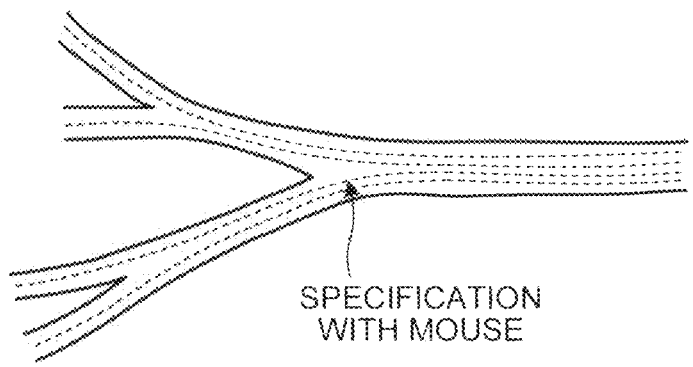
FIG. 8A, FIG. 8B, FIG. 8C, FIG. 9A, FIG. 9B, FIG. 10, FIG. 11, FIG. 12A, FIG. 12B, FIG. 12C, FIG. 13A, FIG. 13B, FIG. 13C, FIG. 14A, FIG. 14B, FIG. 15A and FIG. 15B are views for explaining control of display of a VE moving image performed by the control unit according to the present embodiment.

In first control, the control unit 18 displays a virtual endoscopy image of the lumen having a branch along a running line specified among a plurality of running lines on the monitor 2. In the present embodiment, the control unit 18 displays the virtual endoscopy image of the lumen having the branch along the running line thus specified as a moving image on the monitor 2. As illustrated in FIG. 8A, for example, the operator specifies a running line along which the VE moving image is to be observed with the mouse among the plurality of the running lines superimposed on the synthetic image. The operator then presses "Auto" in the operation menu illustrated in FIG. 7, thereby inputting a request to display the VE moving image. The running lines illustrated in FIG. 8A are depicted by respective dotted lines in different colors.

Figure 8B:
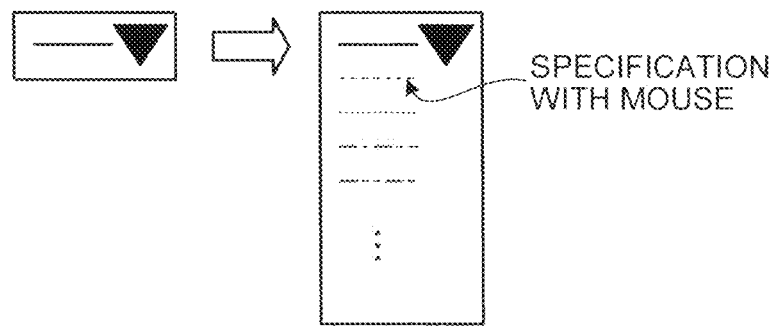

Alternatively, the operator presses a pull-down menu in the operation menu illustrated in FIG. 7 with the mouse. Thus, as illustrated in FIG. 8B, the control unit 18 displays lines in colors corresponding to the respective running lines as selection items in the pull-down menu. The operator specifies a line of a color corresponding to the running line along which observation is to be made with the mouse as illustrated in FIG. 8B. The operator then presses "Auto" in the operation menu illustrated in FIG. 7, thereby inputting a request to display the VE moving image.

Figure 8C:

Thus, the control unit 18 starts display of the VE moving image from one end of the extracted running line corresponding to the running line thus specified toward the other end thereof as illustrated in FIG. 8C. The control unit 18, for example, performs display of the VE moving image from the end on the main duct side of the extracted running line corresponding to the running line thus specified toward the end on the branch side. The control unit 18 causes the virtual endoscopy image generating unit 161a to generate a virtual endoscopy image group in which the position of the viewpoint is moved along the extracted running line corresponding to the running line thus selected. The control unit 18 stores the moving image of the virtual endoscopy image in the internal storage unit 19, for example.

The running line may be automatically specified by the control unit 18. The control unit 18, for example, performs display of the VE moving image in descending order of the length of the extracted running line.

Figure 9A:
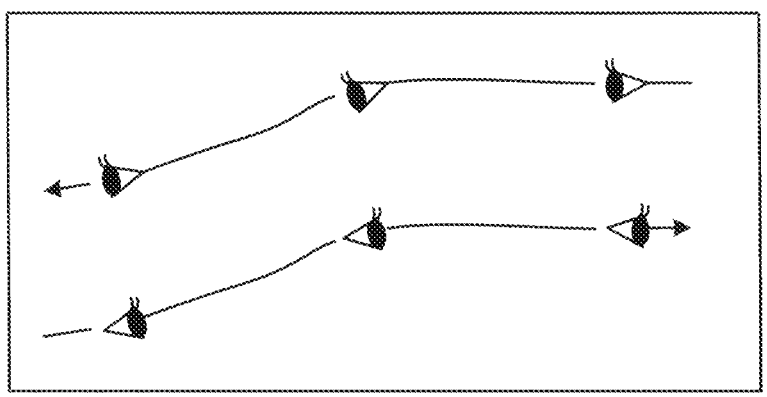
Figure 9B:
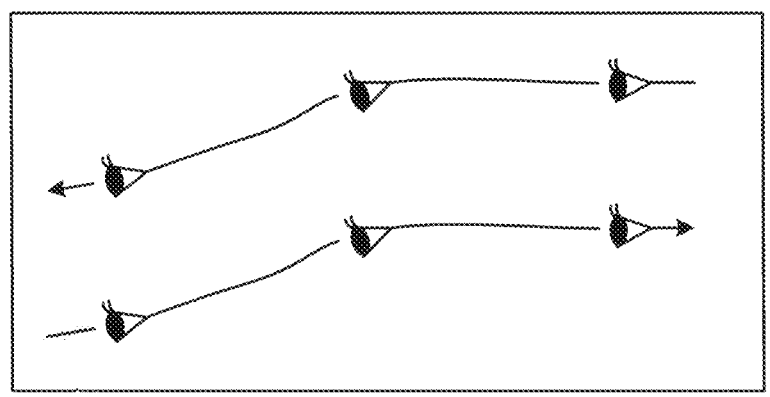

In second control, the control unit 18 displays the virtual endoscopy image by reciprocating a position of a viewpoint along a moving path of a viewpoint. In the present embodiment, to perform the second control, the control unit 18 reciprocates the position of the viewpoint along the moving path of the viewpoint, thereby displaying the virtual endoscopy image as a moving image. To reciprocate the position of the viewpoint, the control unit 18 inverts a visual line direction between an outgoing path and a return path as illustrated in FIG. 9A. Alternatively, the control unit 18 uses a same visual line direction in the outgoing path and the return path as illustrated in FIG. 9B. Performing the method illustrated in FIG. 9B can make display of the moving image of the virtual endoscopy image observed in the virtual endoscopy the same as display of an endoscopy image observed by inserting and extracting an endoscope in an actual endoscopy.

Whether to reciprocate the position of the viewpoint may be set initially or set selectively by the operator. The number of times of reciprocation of the position of the viewpoint may be set initially or set selectively by the operator. In terms of the visual line directions of the outgoing path and the return path in the reciprocation of the position of the viewpoint, one type direction of two types of directions may be set initially or set selectively by the operator. In the case where the reciprocation of the position of the viewpoint is repeated a plurality of times, setting for selecting the two types of visual line directions alternately may be made, for example.

In third control, the control unit 18 controls the image synthesizing unit 162 so as to perform depiction that distinguishes between a range of a running line along which a virtual endoscopy image is displayed and a range of a running line along which no virtual endoscopy image is displayed. In the present embodiment, to perform the third control, the control unit 18 controls the image synthesizing unit 162 so as to perform depiction that distinguishes between a range of a running line along which a virtual endoscopy image is displayed and a range of a running line along which no virtual endoscopy image is displayed.

Figures 10, 11:
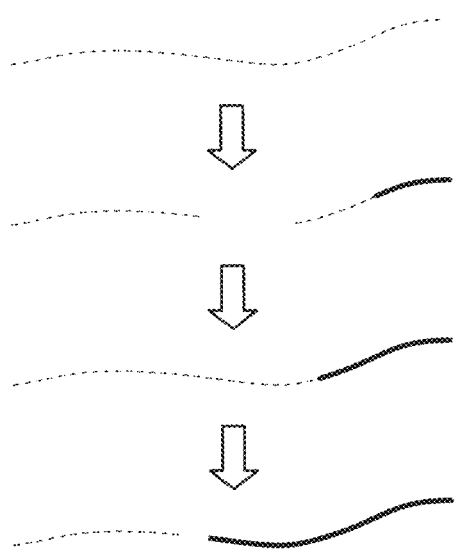

As illustrated in FIG. 10, for example, the control unit 18 controls the image synthesizing unit 162 so as to change a running line along which display of the VE moving image is already performed in the running line depicted by a dotted line from the dotted line to a solid line. This enables the operator to grasp the running line along which display of the VE moving image is already performed simply by referring to the synthetic image on the monitor 2. In the present embodiment, the control unit 18 may change the entire running line along which display of the VE moving image is started from a dotted line to a solid line.

In fourth control, the control unit 18 displays a warning when a termination request is received from the operator in the state where a virtual endoscopy image is displayed along not all of a plurality of running lines. In the present embodiment, to perform the fourth control, the control unit 18 displays a warning when a termination request is received from the operator in the state where the virtual endoscopy image is not displayed as a moving image along all of the plurality of the running lines. When a request to terminate display of the VE moving image is received from the operator at a point when not all the running lines are changed into the solid lines display in the synthetic image, the control unit 18 causes the image synthesizing unit 162 to generate an image of a warning text of "Observation of all running lines is not completed yet! Is it OK to terminate processing?" as illustrated in FIG. 11, for example. Thus, the control unit 18 displays the warning on the monitor 2.

The change of the depiction method may be performed by changing the color of the line. In the same lumen and in another running line that is different from the specified running line, as for a part whose moving paths are common, it may be the case that the display is switched from a dotted line to a solid line, in the another running line. Alternatively, it may be the case that the display of the another running line remains unchanged, that is a dotted line.

In fifth control, the control unit 18 uses a range of a running line specified among the plurality of running lines to display, on the monitor 2, a virtual endoscopy image of the lumen having branches. In the present embodiment, to perform the fifth control, the control unit 18 uses a range of a running line specified among the plurality of the running lines to display the virtual endoscopy image of the lumen having branches as a moving image on the monitor 2.

Figure 12A:
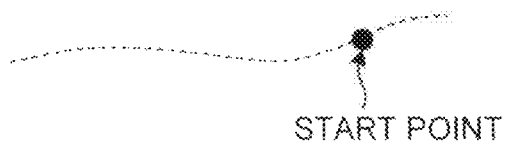

Specifically, the operator specifies a range of a running line along which the VE moving image is to be observed with the mouse among the plurality of the running lines superimposed on the synthetic image. As illustrated in FIG. 12A, for example, the operator sets a start point of a running line along which the VE moving image is to be observed with the mouse. The operator then presses "Start" in the operation menu illustrated in FIG. 7, thereby inputting a request for display of the VE moving image. In this case, under the control of the control unit 18, the virtual endoscopy image generating unit 161a generates a virtual endoscopy image group by moving the position of the viewpoint from a position adjacent to the start point on an extracted running line corresponding to the running line on which the start point is set toward the end on the branch side of the extracted running line. The monitor 2 then displays the virtual endoscopy image group.

Figure 12B:
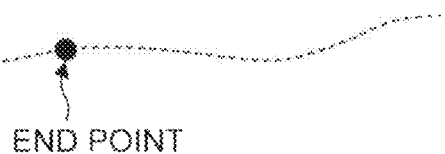

Alternatively, as illustrated in FIG. 12B, the operator sets an end point of the running line along which the VE moving image is to be observed with the mouse. The operator then presses "Start" in the operation menu illustrated in FIG. 7, thereby inputting a request for display of the VE moving image. In this case, under the control of the control unit 18, the virtual endoscopy image generating unit 161a generates a virtual endoscopy image group by moving the position of the viewpoint from the end on the main duct side of the extracted running line corresponding to the running line thus specified toward a position adjacent to the end point thus specified on the extracted running line. The monitor 2 then displays the virtual endoscopy image group.

Figure 12C:
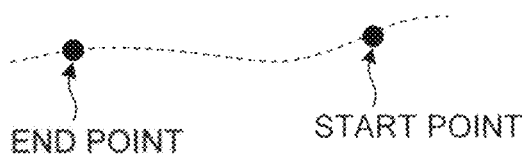

Still alternatively, as illustrated in FIG. 12C, the operator sets a start point and an end point of the running line along which the VE moving image is to be observed with the mouse. The operator then presses "Start" in the operation menu illustrated in FIG. 7, thereby inputting a request for display of the VE moving image. In this case, under the control of the control unit 18, the virtual endoscopy image generating unit 161a generates a virtual endoscopy image group by moving the position of the viewpoint from a position adjacent to the start point thus specified toward a position adjacent to the end point thus specified, on the extracted scanning line corresponding to the running line thus specified. The monitor 2 then displays the virtual endoscopy image group.

In the fifth control for performing display of the VE moving image on the scanning line of the specified range, the control unit 18 may also perform the third control for changing the depiction method on the scanning line along which display of the VE moving image is already performed. Furthermore, in the fifth control, the control unit 18 may also perform the second control for reciprocating the position of the viewpoint.

In sixth control, the control unit 18 controls the image synthesizing unit 162 so as to perform depiction that enables, on a running line of the synthetic image, identification of a position of a viewpoint used for generation of a virtual endoscopy image being currently displayed.

Figure 13A:
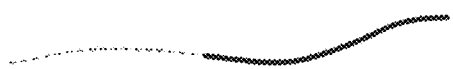

Under the control of the control unit 18, for example, the image synthesizing unit 162 changes a viewpoint range used for display from a dotted line to a solid line as illustrated in FIG. 13A. In other words, the control unit 18 performs processing similar to the control processing described with reference to FIG. 10. The operator can determine the boundary position between the dotted line and the solid line to be the position of the viewpoint used for generation of the virtual endoscopy image being currently displayed. Furthermore, referring to the running line illustrated in FIG. 13A enables the operator to determine the visual line direction to be a direction toward the dotted line.

Figure 13B:
Figure 13C:

Alternatively, under the control of the control unit 18, the image synthesizing unit 162 superimposes a "schematic of an eye" indicating the position of the viewpoint used for generation of the virtual endoscopy image being currently displayed and the visual line direction on the running line as illustrated in FIG. 13B, for example. Still alternatively, under the control of the control unit 18, the image synthesizing unit 162 superimposes an image indicating the position of the viewpoint used for generation of the virtual endoscopy image being currently displayed by a black circle and indicating the visual line direction by an arrow on the running line as illustrated in FIG. 13C, for example.

In seventh control, the control unit 18 performs control for performing depiction that enables identification of a positional relation between a viewpoint used for generation of a virtual endoscopy image being currently displayed and a plurality of branch points included in the lumen on the virtual endoscopy image.

As described above, the control unit 18 acquires the information relating to "the position of the extracted running line in the lumen area, the positions of the branch points of the extracted running line in the lumen area, and the number of branch points of the extracted running line" from the virtual endoscopy image generating unit 161a. Furthermore, the control unit 18 can acquire the correspondence relation between the running line superimposed on the lumen image by the image synthesizing unit 162 and the extracted running line. Thus, the control unit 18 can determine which of the main duct, the first branch, and the second branch the viewpoint used for generation of the virtual endoscopy image being currently displayed is positioned at, for example.

Figure 14A:
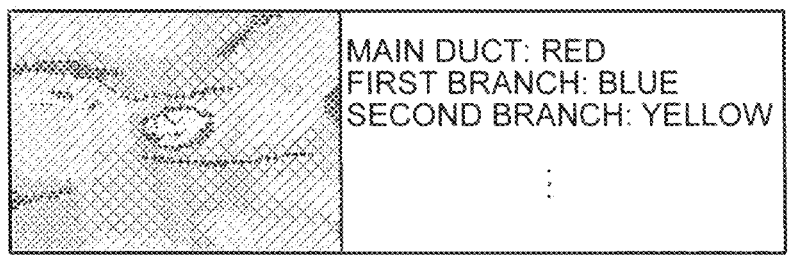

Under the control of the control unit 18 determining that the viewpoint is positioned at the main duct, for example, the virtual endoscopy image generating unit 161a changes the color tone of the virtual endoscopy image being currently displayed to red color tone as illustrated in FIG. 14A. Under the control of the control unit 18 determining that the viewpoint is positioned at the first branch, for example, the virtual endoscopy image generating unit 161a changes the color tone of the virtual endoscopy image being currently displayed to blue color tone as illustrated in FIG. 14A. Under the control of the control unit 18 determining that the viewpoint is positioned at the second branch, for example, the virtual endoscopy image generating unit 161a changes the color tone of the virtual endoscopy image being currently displayed to yellow color tone as illustrated in FIG. 14A in the case where the viewpoint is positioned at the second branch. The control unit 18 changes the color tone of the virtual endoscopy image every time the position of the viewpoint passes through a branch point.

Figure 14B:
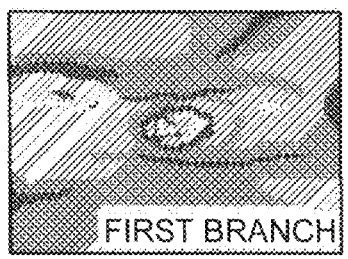

Alternatively, under the control of the control unit 18, the image synthesizing unit 162 synthesizes the position of the viewpoint determined by the control unit 18 at a lower-left part of the display area of the virtual endoscopy image as illustrated in FIG. 14B, for example. The example of FIG. 14B illustrates the fact that the virtual endoscopy image being displayed is a virtual endoscopy image generated with the viewpoint positioned at the "first branch".

In eighth control, the control unit 18 displays a mark on an MPR image obtained by cutting the volume data along a section including a position of a viewpoint used for generation of a virtual endoscopy image specified by an operator during a display of a virtual endoscopy image (during a display of the virtual endoscopy image as a moving image in the present embodiment). In the eighth control, the control unit 18 further displays a mark at a position on a running line corresponding to a position of the viewpoint used for generation of the virtual endoscopy image specified by the operator in the synthetic image.

The operator refers to display of the VE moving image using the scanning line specified by him/herself and presses "Mark" in the operation menu illustrated in FIG. 7 at a point when a virtual endoscopy image depicting an area assumed to be a lesion (hereinafter, an interest image) is displayed, for example. The monitor 2 displays three MPR images passing through the position of the viewpoint used for generation of the interest image. Based on an instruction issued from the control unit 18, the image synthesizing unit 162 performs synthetic processing of the image such that a mark is displayed on at least one display area of the three MPR images displayed on the monitor 2.

Figure 15A:
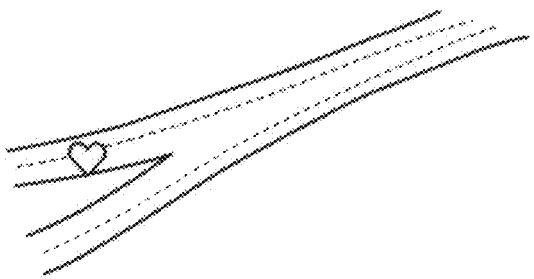

Based on the instruction issued from the control unit 18, for example, the image synthesizing unit 162 synthesizes a mark on a scanning line corresponding to the position of the viewpoint used for generation of the interest image in the synthetic image as illustrated in FIG. 15A.

The control unit 18 stores the moving image of the virtual endoscopy image thus displayed in the internal storage unit 19 as described above. The operator can read the VE moving image thus stored and display the VE moving image again. The operator searches the virtual endoscopy image displayed at point when an MPR image or a synthetic image on which a mark is superimposed appears during a play-back of the moving image, thereby repeatedly observing an area assumed to be a lesion. The play-back of the moving image described above may also be performed in the middle of display of the VE moving image.

Alternatively, in the eighth control, the control unit 18 may perform ninth control to reduce the burden of observing an area assumed to be a lesion (e.g., an area of calcification) again on the operator. In the ninth control, when the mark is specified by an operator, the control unit 18 displays a virtual endoscopy image group using a running line of a certain range including the mark in the running line on which the mark is positioned. In the present embodiment, in the ninth control, the control unit 18 displays a virtual endoscopy image group using a running line of a certain range including the mark in the running line on which the mark set by the operator is positioned as a moving image.

The operator, for example, presses the mark on the synthetic image illustrated in FIG. 15A with the mouse and presses "Start" illustrated in FIG. 7. The control unit 18, for example, displays a virtual endoscopy image group along a certain section in the front and in the rear, with a position on the extracted running line corresponding to the mark on the monitor 2 being the center.

Figure 15B:
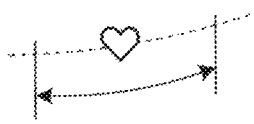

In the ninth control, the control unit 18 may also perform the second control described above. In this case, the control unit 18 displays the VE moving image on the monitor 2 by reciprocation in the certain section as illustrated in FIG. 15B. The control unit 18 inverts the visual line direction between the outgoing path and the return path as illustrated in FIG. 9A. Alternatively, the control unit 18 uses the same visual line direction in the outgoing path and the return path as illustrated in FIG. 9B. In the case where a part of the virtual endoscopy image group along the certain section described above is not stored as a moving image, the control unit 18 causes the virtual endoscopy image generating unit 161*a* to generate a virtual endoscopy image that is yet to be generated.

By performing the ninth control, the operator can repeatedly observe the section in the front of and in the rear of the area assumed to be a lesion in detail by specifying the mark superimposed on the synthetic image of the last frame of the VE moving image.

Figure 16:
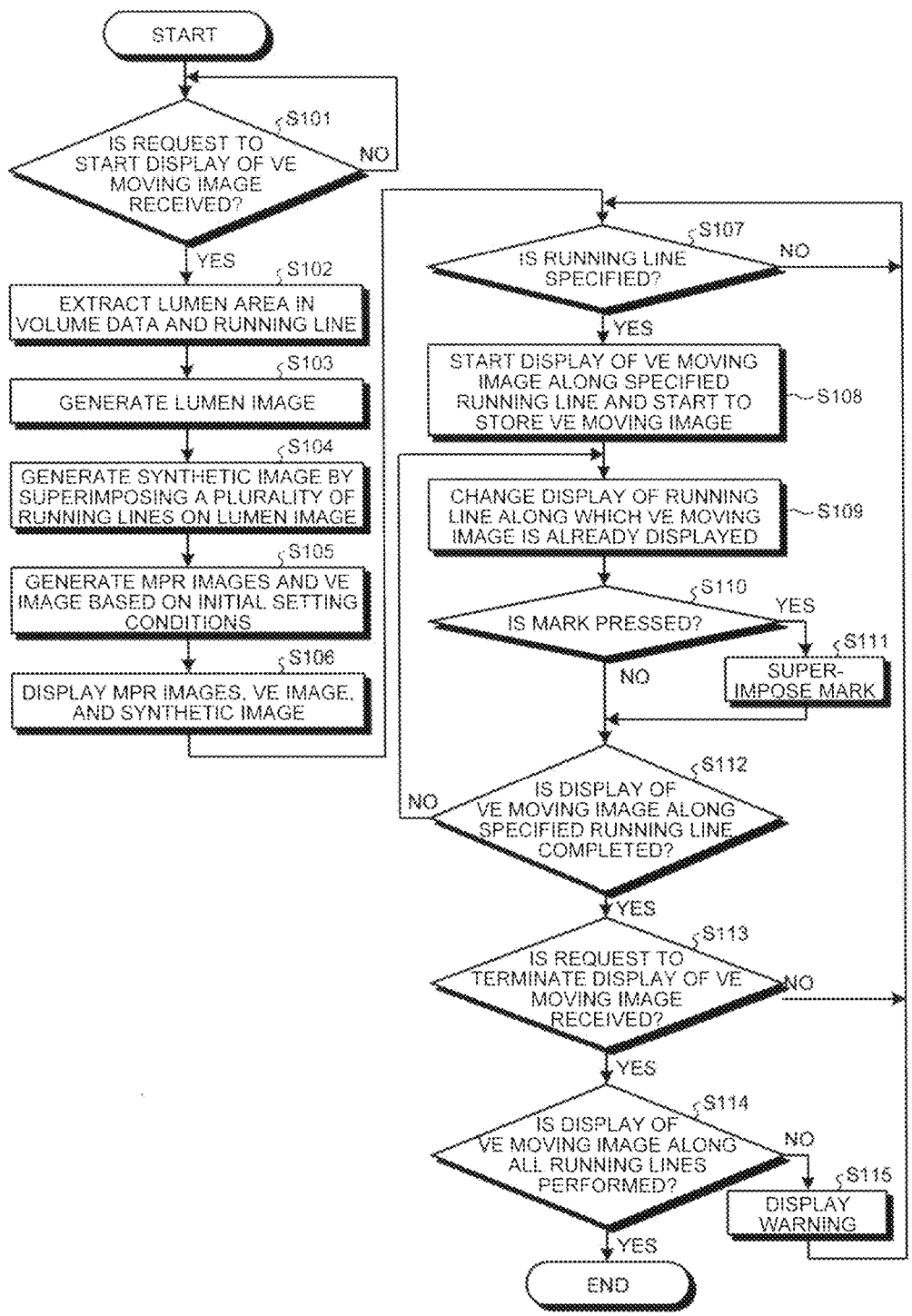
FIG. 16 is a flowchart for explaining exemplary processing of display of a VE moving image performed by the ultrasonic diagnosis apparatus according to the present embodiment.
Figure 17:
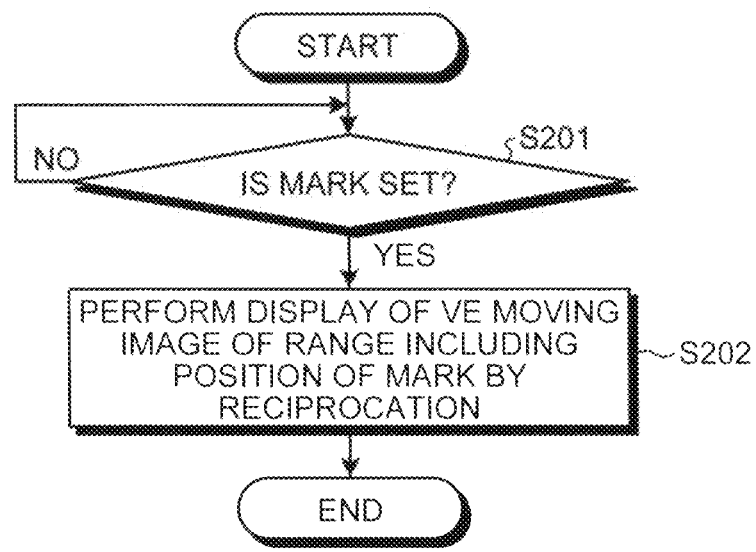
FIG. 17 is a flowchart for explaining exemplary play-back processing of a VE moving image performed by the ultrasonic diagnosis apparatus according to the present embodiment.

The following describes the processing of the ultrasonic diagnosis apparatus according to the present embodiment with reference to FIG. 16 and FIG. 17. FIG. 16 is a flowchart for explaining exemplary processing of display of a VE moving image performed by the ultrasonic diagnosis apparatus according to the present embodiment. FIG. 17 is a flowchart for explaining exemplary play-back processing of a VE moving image performed by the ultrasonic diagnosis apparatus according to the present embodiment.

As illustrated in FIG. 16, the control unit 18 of the ultrasonic diagnosis apparatus according to the present embodiment determines whether a request to start display of a VE moving image of a lumen having branches included in volume data is received (Step S101). When no request to start display of a VE moving image is received (No at Step S101), the control unit 18 waits until a request to start display of a VE moving image is received.

By contrast, when a request to start display of a VE moving image is received (Yes at Step S101), the virtual endoscopy image generating unit 161*a* extracts a lumen area in the volume data and extracts a running line (an extracted running line) (Step S102). The lumen image generating unit 161*b* generates a lumen image (Step S103). The image synthesizing unit 162 generates a synthetic image by superimposing a plurality of running lines on the lumen image (Step S104). The MPR image generating unit 161*c* generates MPR images (the A surface, the B surface, and the C surface), and the virtual endoscopy image generating unit 161*a* generates a virtual endoscopy image based on the initial setting conditions (Step S105). The monitor 2 displays the MPR images, the virtual endoscopy image, and the synthetic image under the control of the control unit 18 (Step S106).

The control unit 18 determines whether a running line in the synthetic image is specified (Step S107). When no running line is specified (No at Step S107), the control unit 18 waits until a running line is specified.

By contrast, when a running line is specified (Yes at Step S107), the control unit 18 starts display of a VE moving image along the running line thus specified and starts storing the VE moving image (Step S108). In the case where a range of display of the VE moving image is specified in the running line specified by the operator, display of the VE moving image started at Step S108 is performed only on the range thus specified.

The control unit 18 changes display of a running line along which the VE moving image is already displayed (Step S109). At Step S109, the control unit 18 may perform display that can identify the position of the viewpoint of the virtual endoscopy image being displayed as a VE moving image. The control unit 18 determines whether "Mark" in the operation menu is pressed (Step S110). When "Mark" is pressed (Yes at Step S110), the control unit 18 superimposes a mark on the MPR images and the synthetic image (Step S111).

After the processing at Step S111 or when "Mark" is not pressed (No at Step S110), the control unit 18 determines whether display of the VE moving image along the running line thus specified is completed (Step S112). If display of the VE moving image along the running line thus specified is not completed (No at Step S112), the control unit 18 returns to Step S109, and performs the control for changing display of a running line along which the VE moving image is already displayed.

By contrast, if display of the VE moving image along the running line thus specified is completed (Yes at Step S112), the control unit 18 determines whether a request to terminate display of the VE moving image is received (Step S113). When no request to terminate display of the VE moving image is received (No at Step S113), the control unit 18 returns to Step S107, and determines whether another running line is specified.

By contrast, when a request to terminate display of the VE moving image is received (Yes at Step S113), the control unit 18 determines whether display of the VE moving image along all the running lines is performed (Step S114). When display of the VE moving image along all the running lines is not performed (No at Step S114), the control unit 18 displays a warning (Step S115). Subsequently, the control unit 18 returns to Step S107, and determines whether another running line is specified.

By contrast, when display of the VE moving image along all the running lines is performed (Yes at Step S114), the control unit 18 terminates the control processing of display of the VE moving image.

To perform play-back processing of the VE moving image, the control unit 18 determines whether a mark is specified as illustrated in FIG. 17 (Step S201). If no mark is specified (No at Step S201), the control unit 18 waits until a mark is specified.

By contrast, if no mark is specified (Yes at Step S201), the control unit 18 performs display of the VE moving image of a range including the position of the mark thus specified by reciprocation (Step S202). Thus, the control unit 18 terminates the play-back processing of the VE moving image.

As described above, the present embodiment displays a synthetic image obtained by superimposing, on a lumen image, a plurality of running lines indicating moving paths of the position of the viewpoint. By referring to the synthetic image, the operator can grasp information for completing observation of the entire lumen having branches, such as the shape of the moving path of the viewpoint along which display of a VE moving image is performed and the number of moving paths of the viewpoint along which display of the VE moving image is performed. As a result, the present embodiment can facilitate the operator's grasping of completion of the observation of the lumen having branches.

In the present embodiment, performing the first control and the fifth control enables the operator to display the VE moving image of a plurality of paths sequentially by a simple operation to specify a running line or a range on a running line. In the present embodiment, performing the third control can facilitate the operator's grasping of a path along which display of the VE moving image is not performed yet, thereby preventing an oversight in observation. In the present embodiment, performing the sixth control can facilitate the operator's grasping of the position inside of the lumen depicted in the virtual endoscopy image displayed as the VE moving image.

In the present embodiment, performing the seventh control can facilitate the operator's grasping of what number branch of the lumen the moving viewpoint is currently positioned at. In the present embodiment, performing the second control enables the operator to repeatedly observe the same path in detail. In the present embodiment, because the control for reversing the visual line direction is performed in the second control, the operator can repeatedly observe the same path in detail in different directions. In the present embodiment, because the control for fixing the visual line direction is performed in the second control, the operator can repeatedly observe the same path in detail in the visual line direction identical to that of an endoscope used in an endoscopy. In the present embodiment, a warning displayed by performing the fourth embodiment enables the operator to complete the observation of the lumen having branches for sure.

In the present embodiment, performing the eighth control and the ninth control can facilitate the operator to display, any number of times, the VE moving image of a range of the lumen where detailed observation is required. Furthermore, the operator can grasp the position of a lesion by referring to the position of a mark on the MPR images of orthogonal three sections and the synthetic image on which the mark is superimposed. In other words, the present embodiment can provide information for determining a treatment plan (e.g., whether to save the nipple).

In the present embodiment, the plurality of the running lines superimposed on the lumen image may be set by the operator. In this case, the operator makes a request for setting of the running lines via the input device 3. The control unit 18 displays a lumen image on the monitor 2. The operator refers to the lumen image, thereby setting a plurality of running lines on the lumen image with the mouse or the like included in the input device 3. Thus, the image synthesizing unit 162 generates the synthetic image illustrated in FIG. 6B. In this case, the plurality of the running lines set on the lumen image by the operator are used as the moving path of the position of the viewpoint in display of the VE moving image described above. In the present embodiment, the operator may modify and delete all or a part of the running lines depicted in the synthetic image or add another running line to the synthetic image.

Figure 18:
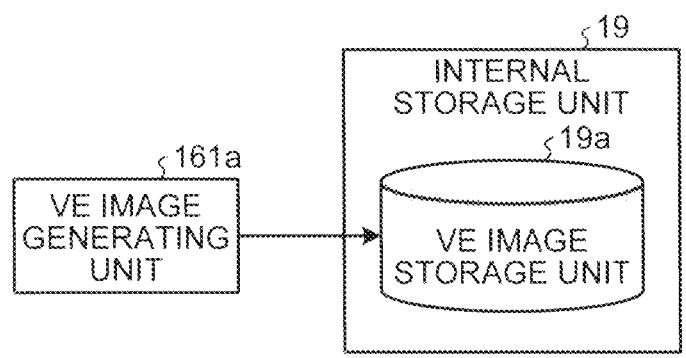
FIG. 18 is a view for explaining a modification of the present embodiment.

In the present embodiment, when a request for display is received, the control unit 18 causes the virtual endoscopy image generating unit 161*a* to generate a virtual endoscopy image group corresponding to the request from volume data. In the present embodiment, when a request for display of a moving image is received, the control unit 18 causes the virtual endoscopy image generating unit 161*a* to generate a virtual endoscopy image group corresponding to the request from volume data. In other words, in the present embodiment, because the virtual endoscopy image generating unit 161*a* needs to perform volume rendering processing in real time, the load may possibly be increased. To reduce the processing load on the virtual endoscopy image generating unit 161*a*, a modification described below may be employed in the present embodiment. FIG. 18 is a view for explaining the modification of the present embodiment.

In the modification of the present embodiment, the virtual endoscopy image generating unit 161*a* generates a virtual endoscopy image group to be displayed using the plurality of the running lines in advance and stores the virtual endoscopy image group in a virtual endoscopy image storage unit 19*a* included in the internal storage unit 19 as illustrated in FIG. 18. In the present modification, the virtual endoscopy image generating unit 161*a* generates virtual endoscopy image groups to be displayed as a moving image using the plurality of the running lines in advance and stores the virtual endoscopy image group in the virtual endoscopy image storage unit 19*a* included in the internal storage unit 19. When a request for display is received, the control unit 18 selects a virtual endoscopy image group corresponding to the request from the virtual endoscopy image storage unit 19*a* and displays the virtual endoscopy image group on the monitor 2. In the present modification, when a request for display of a moving image is received, the control unit 18 selects a virtual endoscopy image group corresponding to the request from the virtual endoscopy image storage unit 19*a* and displays the virtual endoscopy image group as a moving image on the monitor 2.

In the modification of the present embodiment, the virtual endoscopy image groups to be used for display of the VE moving image are comprehensively generated in advance. This can reduce the load on the ultrasonic diagnosis apparatus and enable display of the VE moving image smoothly.

In the embodiment and the modification, the position of the viewpoint is automatically moved along the running line specified by the operator, and the virtual endoscopy image is displayed as a moving image. In the embodiment and the modification, however, formation of displaying of the virtual endoscopy image is not limited to automatic displaying of a moving image. The formation of displaying of the virtual endoscopy image may be parallel displaying of a plurality of virtual endoscopy images generated by a plurality of viewpoints on the running line, for example.

Furthermore, movement of the position of the viewpoint on the running line may be performed by a manual operation performed by the operator. In this case, the control unit 18 moves a position of a viewpoint along the running line thus specified in response to an operation performed by an operator with an input device 3 and displays a virtual endoscopy image of the lumen having the branch (virtual endoscopy image of the lumen of the mammary gland) on the monitor 2. The operator, for example, specifies a running line and rotates the wheel of the mouse or the trackball. Based on the amount of rotation and the direction of rotation performed by the operator, the control unit 18 moves the position of the viewpoint on the running line specified by the operator. The control unit 18 then displays a virtual endoscopy image corresponding to the position of the viewpoint thus moved. Such a manual operation enables the operator to sequentially observe virtual endoscopy images viewed from different positions of viewpoints at intervals desired by him/herself and to perform an image diagnosis of calcification or the like in detail. Furthermore, by inverting the direction of rotation of the wheel of the mouse and the trackball, the operator can make the observation described with reference to FIG. 9A and FIG. 9B. The contents described in the embodiment and the modification are applicable to the present modification except that movement of the position of the viewpoint on the running line is performed by a manual operation performed by the operator.

In the embodiment and the modification, a mammary gland is explained as an example of a lumen having branches. The image processing method described in the present embodiment and the modification is applicable to an arbitrary organ as long as it is a lumen that has branches and that can be depicted in an ultrasonic image, such as a carotid artery. In the embodiment and the modification, the image processing method described above is performed by the ultrasonic diagnosis apparatus. The image processing method described in the present embodiment may be performed by a medical image diagnosis apparatus that can acquire volume data including a lumen having branches, such as an X-ray diagnosis apparatus, an X-ray CT apparatus, and an MRI apparatus.

The image processing method described in the present embodiment and the modification may be performed by an image processing apparatus provided independently of the medial image diagnosis apparatus. Specifically, the image processing apparatus has the functions of the volume data processing unit 16 and the control unit 18 illustrated in FIG. 1. The image processing apparatus receives volume data that is three-dimensional medical image data and that includes a lumen having branches from a database of picture archiving and communication systems (PACS) serving as a system that manages data of various types of medical images and a database of an electronic medical record system that manages electronic medical records to which medical images are attached, for example. The image processing apparatus performs the image processing method described in the present embodiment and the modification.

In the present embodiment and the modification, the components of the devices illustrated in the drawings are functional and conceptual components and are not necessarily required to be physically configured as illustrated in the drawings. In other words, a specific form of distribution and integration of the devices is not limited to that illustrated in the drawings. A part or all of the devices may be functionally or physically distributed and integrated in arbitrary units depending on various types of loads and states of use. The processing performed by the image synthesizing unit 162, for example, may be performed by the image generating unit 15. Furthermore, all or an arbitrary part of the processing functions performed by the devices can be realized by a CPU and a computer program analyzed and executed by the CPU or realized as hardware by wired logic.

The image processing method described in the present embodiment and the modification can be realized by a computer, such as a personal computer and a workstation, executing an image processing program prepared in advance. The image processing program may be distributed over a network such as the Internet. Furthermore, the image processing program may be recorded in a computer-readable recording medium, such as a hard disk, a flexible disk (FD), a compact disc read-only memory (CD-ROM), a magneto-optical disc (MO), and a digital versatile disk (DVD), and executed by a computer reading the image processing program from the recording medium.

As described above, the present embodiment and the modification can facilitate grasping of completion of observation of a lumen having branches and store image data useful for an image diagnosis for sure.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
processing circuitry that
generates a lumen image depicting a shape of a lumen having a branch, based on volume data that is three-dimensional medical image data;
generates a plurality of running lines based on a shape of the lumen having the branch;
generates a synthetic image by superimposing, on the lumen image, the plurality of the running lines indicating moving paths of a viewpoint in a virtual endoscopy image of the lumen having the branch;
displays the synthetic image on a display; and
performs depiction that distinguishes between a first section of a running line, of the plurality of running lines, along which a virtual endoscopy image has been displayed as a moving image by moving a viewpoint along the running line of the lumen and a second section of the running line along which no virtual endoscopy image has been displayed as the moving image,
wherein the processing circuitry displays the virtual endoscopy image of the lumen having the branch along the running line, which is specified among the plurality of the running lines on the display, displays a first mark on a section image obtained by cutting the volume data along a section including a position of the viewpoint used for generation of the virtual endoscopy image specified by an operator, and displays a second mark at a position on the running line corresponding to the position of the viewpoint used for generation of the virtual endoscopy image in the synthetic image during a display of the virtual endoscopy image.

2. The medical image diagnosis apparatus according to claim 1, wherein the volume data used to generate the lumen image by the processing circuitry is three-dimensional medical image data relating to a mammary gland.

3. The medical image diagnosis apparatus according to claim 1, wherein the processing circuitry displays a warning when a termination request is received from an operator in a state where the virtual endoscopy image has been displayed along not all of the running lines.

4. The medical image diagnosis apparatus according to claim 1, wherein the processing circuitry uses the first section of the running line specified among the plurality of running lines to display, on the display, a virtual endoscopy image of the lumen having the branch.

5. The medical image diagnosis apparatus according to claim 1, wherein the processing circuitry controls the image synthesizing circuitry so as to perform depiction that enables, on the running line of the synthetic image, identification of a position of the viewpoint used for generation of a virtual endoscopy image being currently displayed.

6. The medical image diagnosis apparatus according to claim 1, wherein the processing circuitry performs control for performing depiction that enables identification of a positional relation between the viewpoint used for generation of a virtual endoscopy image being currently displayed and a plurality of branch points included in the lumen on the virtual endoscopy image.

7. The medical image diagnosis apparatus according to claim 1, wherein the processing circuitry displays, when the mark is specified by an operator, a virtual endoscopy image group using the running line of a section including the mark.

8. The medical image diagnosis apparatus according to claim 1, wherein the processing circuitry displays the virtual endoscopy image by reciprocating a position of the viewpoint along a moving path of the viewpoint and inverts a visual line direction between an outgoing path and a return path or uses a same visual line direction in the outgoing path and the return path.

9. The medical image diagnosis apparatus according to claim 1, further comprising:
virtual endoscopy image generating circuitry that generates the virtual endoscopy image, wherein
when a request for display is received, the processing circuitry causes the virtual endoscopy image generating circuitry to generate, from the volume data, a virtual endoscopy image group corresponding to the request.

10. The medical image diagnosis apparatus according to claim 1, further comprising:
virtual endoscopy image generating circuitry that generates the virtual endoscopy image, wherein
the virtual endoscopy image generating circuitry generates a virtual endoscopy image group to be displayed using the plurality of the running lines in advance and stores the virtual endoscopy image group in a memory, and
when a request for display is received, the processing circuitry selects the virtual endoscopy image group corresponding to the request from the memory and displays the virtual endoscopy image group on the display.

11. The medical image diagnosis apparatus according to claim 1, wherein the processing circuitry displays the virtual endoscopy image of the lumen having the branch along the running line thus specified as a moving image on the display.

12. The medical image diagnosis apparatus according to claim 1, wherein the processing circuitry moves a position of the viewpoint along the running line thus specified in response to an operation performed by an operator with an input device, and displays the virtual endoscopy image of the lumen having the branch on the display.

13. An image processing apparatus, comprising:
processing circuitry that
generates a lumen image which depicts a shape of a lumen having a branch and which is based on volume data that is three-dimensional medical image data;
generates a plurality of running lines, based on a shape of the lumen having the branch;
generates a synthetic image by superimposing, on the lumen image, the plurality of the running lines indicating moving paths of a viewpoint in a virtual endoscopy image of the lumen having the branch;
displays the synthetic image on a display; and
performs depiction that distinguishes between a first section of a running line, of the plurality of running lines, along which a virtual endoscopy image has been displayed as a moving image by moving a viewpoint along the running line of the lumen and a second section of the running line along which no virtual endoscopy image has been displayed as the moving image,
wherein the processing circuitry displays the virtual endoscopy image of the lumen having the branch along the running line, which is specified among the plurality of the running lines on the display, displays a first mark on a section image obtained by cutting the volume data along a section including a position of the viewpoint used for generation of a virtual endoscopy image specified by an operator, and displays a second mark at a position on the running line corresponding to the position of the viewpoint used for generation of the virtual endoscopy image in the synthetic image during a display of the virtual endoscopy image.

14. An image processing method, comprising:
generating a lumen image depicting a shape of a lumen having a branch based on volume data that is three-dimensional medical image data;
generating a plurality of running lines based on a shape of the lumen having the branch;
generating a synthetic image by superimposing, on the lumen image, the plurality of the running lines indicating moving paths of a viewpoint in a virtual endoscopy image of the lumen having the branch; and
displaying the synthetic image on a display, wherein
the displaying step includes performing depiction that distinguishes between a first section of a running line, of the plurality of running lines, along which a virtual endoscopy image has been displayed as a moving image by moving a viewpoint along the running line of the lumen and a second section of the running line along which no virtual endoscopy image has been displayed as the moving image; and
the displaying step includes displaying the virtual endoscopy image of the lumen having the branch along the running line, which is specified among the plurality of the running lines on the display, displaying a first mark on a section image obtained by cutting the volume data along a section including a position of the viewpoint used for generation of a virtual endoscopy image specified by an operator, and displaying a second mark at a position on the running line corresponding to the position of the viewpoint used for generation of the virtual endoscopy image in the synthetic image during a display of the virtual endoscopy image.

* * * * *